United States Patent
Lundgren et al.

(10) Patent No.: US 6,238,536 B1
(45) Date of Patent: May 29, 2001

(54) ARRANGEMENT FOR ANALYSIS OF EXHAUST GASES

(75) Inventors: Staffan Lundgren, Hindås; Edward Jobson, Romelanda; Ulf Ärlig, Kållered; Per Salomonsson, Göteborg; Anders Unosson, Göteborg; Ove Hjortsberg, Göteborg, all of (SE)

(73) Assignee: AB Volvo, Göteborg (SE)

( * ) Notice: Subject to any disclaimer, the term of this patent is extended or adjusted under 35 U.S.C. 154(b) by 0 days.

(21) Appl. No.: 08/894,391

(22) PCT Filed: Feb. 21, 1996

(86) PCT No.: PCT/SE96/00235

§ 371 Date: Sep. 8, 1997

§ 102(e) Date: Sep. 8, 1997

(87) PCT Pub. No.: WO96/26434

PCT Pub. Date: Aug. 29, 1996

(30) Foreign Application Priority Data

Feb. 21, 1995 (SE) .................................................. 9500632

(51) Int. Cl.[7] .................................................. G01N 27/407
(52) U.S. Cl. ......................... 204/426; 204/425; 205/781
(58) Field of Search ................................. 204/421–429, 204/412; 205/781

(56) References Cited

U.S. PATENT DOCUMENTS

| | | | |
|---|---|---|---|
| 3,556,950 | * | 1/1971 | Dahms .................................. 204/419 |
| 4,452,682 | * | 6/1984 | Takata et al. ......................... 204/416 |
| 4,591,422 | | 5/1986 | Kato et al. . |
| 4,927,517 | | 5/1990 | Mizutani et al. . |
| 5,339,627 | | 8/1994 | Baier . |
| 5,352,353 | | 10/1994 | Schönauer et al. . |
| 5,397,442 | * | 3/1995 | Wachsman ........................... 204/428 |
| 5,482,609 | * | 1/1996 | Kobayashi et al. .................. 204/424 |
| 5,736,028 | | 4/1998 | Hjortsberg et al. . |

FOREIGN PATENT DOCUMENTS

| | | |
|---|---|---|
| 35 04 498 C2 | 4/1989 | (DE) . |
| 42 28 052 A1 | 4/1993 | (DE) . |
| 7844330 | 6/1980 | (GB) . |
| 8700712 | 7/1987 | (GB) . |
| 92/14143 | 8/1992 | (WO) . |
| 94/00468 | 11/1994 | (WO) . |

* cited by examiner

Primary Examiner—T. Tung
(74) Attorney, Agent, or Firm—Royston, Rayzor, Vickery, Novak & Druce, L.L.P.

(57) ABSTRACT

Exhaust gas analyzers are disclosed for analyzing the exhaust gases from a combustion process including a sensor unit mounted for direct contact with the exhaust gases in which the sensor unit includes a number of sensors such as lambda sensors, $NO_x$ sensors, oxygen sensors, and residual heat sensors, mounted on a common substrate for detecting specific gases and temperatures in the exhaust gases and generating signals based thereon, the substrate being an oxygen-ion-conductive ceramic material and the sensors elements including conductive patterns applied to the common substrate, and a common analyzer connected to the sensor units for analyzing the signals generated by the sensor elements.

15 Claims, 4 Drawing Sheets

ARRANGEMENT FOR ANALYSIS OF EXHAUST GASES

FIELD OF THE INVENTION

The present invention relates to an arrangement for analyzing exhaust gases from a combustion process.

BACKGROUND OF THE INVENTION

In the field of motor vehicle combustion engines, there is a desire to have the ability to detect the concentration of different gaseous components in the exhaust gas stream from the engine. Such measurements can be used for controlling the operation of a combustion engine, with a view toward optimizing the amounts of injected fuel and air. If the engine can be provided with an optimal composition of the fuel/air mixture during all operating conditions, the fuel consumption and the harmful emissions from the combustion engine can be minimized.

In addition to engine control, such gas measurement should also provide the ability to be used in connection with a diagnosis of a vehicle's catalytic converter (catalyzer). In this context, the fuel and oxygen levels must lie within certain ranges in order that the vehicle's catalyzer should be able to operate optimally. A measure of the catalyzer's so-called "light-off" time, i.e. the time which elapses before the catalyzer purifies the exhaust gases optimally, can also be used during a diagnosis of the catalyzer's operation.

Different forms of gas sensors are known for achieving the above-mentioned objectives. One example of such a gas sensor, which is particularly for use in connection with motor vehicles, is the so-called lambda sensor, by means of which the oxygen content in the exhaust gases can be detected. The signal from a lambda sensor can be used in connection with optimizing the fuel and oxygen supply to the engine. In addition to the oxygen, it would be desirable to detect other components in the exhaust gases. Examples of known sensors (apart from lambda sensors) are thermistors, $NO_x$ sensors (i.e. sensors for nitrogen oxide compounds), oxygen sensors, carbon monoxide sensors and residual heat sensors.

An arrangement for detecting combustible gaseous hydrocarbons by means of a measurement bridge which has pellistors (pellet resistors) is known from British Patent No. 2,185,579. A pellistor is a resistor with a temperature-dependent resistance, as described in British Patent No. 2,044,937, for example. An application of pellistors in connection with the detection of exhaust gases in motor vehicles is described in Swedish Patent Application No. 9301715-0.

In connection with the measuring and detecting of different gas components in the exhaust gas stream from a combustion engine, a problem exists in that measurement signals from certain of the above-mentioned sensors can be influenced by other gases than those for which the sensor is intended. For example, the $NO_x$ sensor (apart from sensing the concentration of nitrogen oxide compounds) can also be sensitive to the concentration of oxygen and hydrocarbons. By using a plurality of different types of sensors at the same time, it should thus be possible to separate out each of the different gas components and, despite the cross-sensitivity of the different sensors, obtain a measurement of the composition of the measured gas. Using a plurality of different sensors in this way is, however, expensive and requires space. Each separate gas sensor requires a probe, a fixture, cabling, possibly an amplifier, an analyzer unit and a common analyzer unit which, from the signals of the different sensors, produces output signals giving the composition of the measured gas.

SUMMARY OF THE INVENTION

In accordance with the present invention, these and other objects have now been realized by the invention of apparatus for analyzing exhaust gases from a combustion process which comprises at least one sensor unit mounted for direct contact with the exhaust gases, the at least one sensor unit comprising a plurality of sensor elements mounted on a common substrate for detecting specific gases contained in the exhaust gases and generating signals based thereon, the substrate comprising an oxygen-ion-conductive ceramic material and the plurality of sensor elements comprising conductive patterns applied to the common substrate, and a common analyzer unit connected to the at least one sensor unit for analyzing the signals generated by the plurality of sensor elements. Preferably, the plurality of sensor elements include lambda sensors, $NO_x$ sensors, oxygen sensors, and residual heat sensors.

In accordance with one embodiment of the apparatus of the present invention, the common substrate comprises stabilized zirconium dioxide or titanium oxide. In one preferred embodiment, the $NO_x$ sensor includes oxygen-ion-transport means whereby the $NO_x$ sensor generates the signal based substantially only on the $NO_x$ content of the exhaust gases and substantially independent of the oxygen content of the exhaust gases. In a preferred embodiment, the oxygen-ion-transport means comprises the conductive pattern including a first conductive pattern comprising an anode, a second conductive pattern comprising a cathode, an external voltage source for driving a current comprising the oxygen ions, and current measuring means for measuring the current so as to provide the signal as a measure of the concentration of the NOx-compounds in the exhaust gases. Preferably, at least one of the anode and the cathode comprises gold.

In accordance with another embodiment of the apparatus of the present invention, the residual heat sensor comprises a first resistor including a surface exposed to the exhaust gases whereby the first resistor increases its temperature dependent resistance when heated in the presence of oxidizable gas components in the exhaust gases, and the second resistor, a measuring bridge connected to the residual heat sensor, and a voltage source for supplying a voltage to the measuring bridge. Preferably, the second resistor comprises a reference for comparison with the resistance of the first resistor.

In accordance with another embodiment of the apparatus of the present invention, the apparatus includes heating means for heating the common substrate. Preferably, the heating means comprises a heating wire mounted in the substrate, and including a voltage source connected to the heating wire.

In accordance with another embodiment of the apparatus of the present invention, the apparatus includes a protective cap substantially covering the at least one sensor unit.

In accordance with another embodiment of the apparatus of the present invention, at least one of the lambda sensors, $NO_x$ sensors and oxygen sensors comprises at least one of the plurality of sensor units, and the at least one of the lambda sensor, the $NO_x$ sensor and the oxygen sensor includes an associated air gap in the common substrate, a first electrode formed in the air gap, and a second electrode formed on the common substrate exposed to the exhaust gases.

In accordance with another embodiment of the apparatus of the present invention, the plurality of sensor units comprises a lambda sensor and a residual heat sensor, whereby the apparatus can be used for diagnosis of a catalyzer for purification of the exhaust gases. Preferably, the apparatus includes an associated air gap within the common substrate, and an electrode associated with the lambda sensor arranged in the air gap.

In accordance with another embodiment of the apparatus of the present invention, the plurality of sensor units includes at least one $NO_x$ sensor and a residual heat sensor whereby the apparatus can be used for analyzing the exhaust gases from a diesel engine. Preferably, the apparatus further comprises an oxygen sensor.

It has thereby been found that by placing a number of these sensors on one or more common substrates and by arranging the sensor elements in an integrated "multisensor" with a single attachment fixture, as well as common cabling, amplifier unit and analyzer unit, an analysis of the different gas components in the gas mixture present is possible.

BRIEF DESCRIPTION OF THE DRAWINGS

The invention may be more fully appreciated with reference to the following detailed description, which, in turn, refers to the Figures in which.

DETAILED DESCRIPTION

Figure 1:
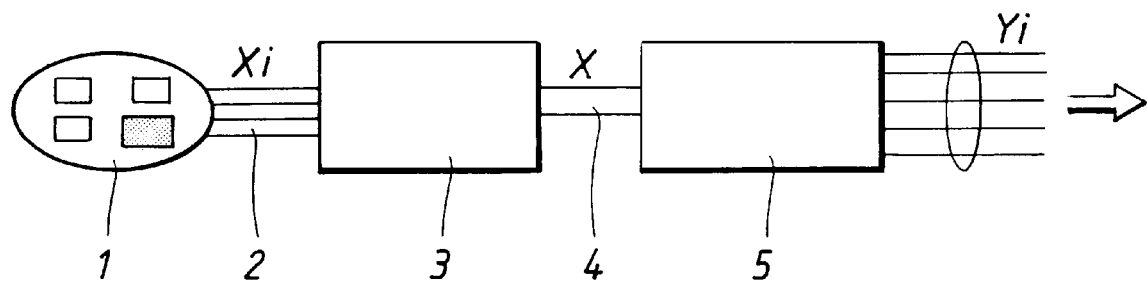
FIG. 1 is a schematic representation of a measuring system for use in accordance with the present invention.

Referring to the drawings, in which like reference numerals refer to like elements thereof, FIG. 1 schematically shows an arrangement which includes the present invention. According to a preferred embodiment, the arrangement comprises a sensor unit 1 consisting of a plurality of sensors, i.e. an integrated "multisensor," which is intended to be placed in the exhaust outlet of a motor vehicle. In accordance with the description which follows, the sensor unit 1 can comprise sensors for detecting NOx-compounds (nitrogen oxide compounds) and oxygen. The sensor unit 1 can further comprise a residual heat sensor which is composed of a known pellistor, a temperature sensor and a lambda sensor. Each separate sensor which is included in the sensor unit 1 emits a signal $X_i$, where i=1, 2, ... n.

The signals $X_i$ supplied from the sensor unit 1 are supplied by cabling 2 to a measuring unit in the form of a filter- and amplifier-unit 3 which comprises filter and amplifier circuits for treatment of the respective signals $X_i$. The treated signal packet X is supplied to an analyzer unit 5 by means of second cabling 4, unit 5 preferably being computer-based, in order to produce a measurement of the temperature and of the amounts of the gas components which are detected by the sensors in the sensor unit 1. The analyzer unit can be made according to the principle of template-recognition (pattern-recognition), e.g. of the neuro-net type. The signal packet X from the sensor unit 1, the signals $X_i$ constitute a resolvable combination of the size of the different gas components. With the aid of suitably-chosen algorithms, the analyzer unit 5 can break down the signal packet X into its components $Y_i$ from the respective signals $X_i$ of the sensor unit 1.

A number of measurement signals $Y_i$ is supplied from the analyzer unit 5, said signals providing a measure of the different substances which have been detected by the sensor unit 1, e.g. concerning the concentration of oxygen and $NO_x$-compounds and the temperature. These signals are then supplied to the vehicle's control system and are used for controlling the operation of the engine as well as for diagnosis of the catalyzer's operation.

Figure 2:
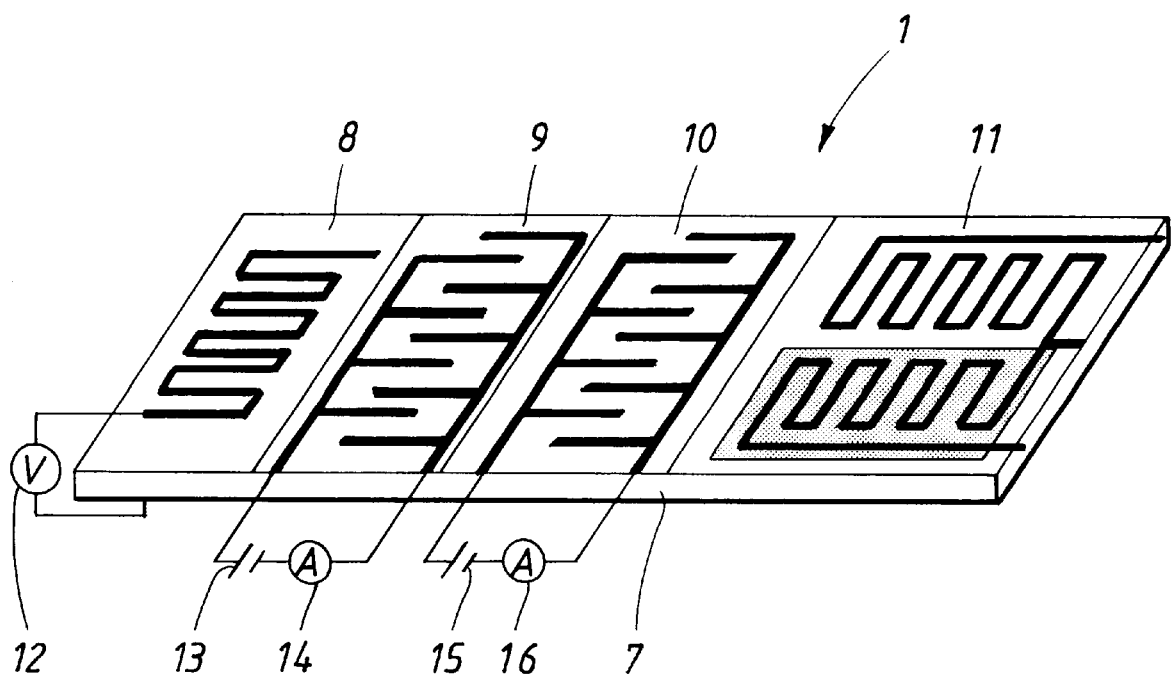
FIG. 2 is a top, perspective, partially schematic view of a sensor unit in accordance with the present invention.

FIG. 2 shows a detailed view of a sensor unit 1 which is intended to be placed in the gas stream in the exhaust system of a motor vehicle. The sensor unit 1 comprises a substrate 7 which is common for all of the included sensors. The substrate 7 comprises, in accordance with this embodiment, oxygen-ion-conductive zirconium-dioxide, $ZrO_2$, which is stabilized, i.e. "fixed" in a certain crystal structure which is advantageous with respect to the conductivity for oxygen ions. Yttrium-oxide can preferably be used as a stabilizer. A lambda probe 8, an $NO_x$-sensor 9, an oxygen sensor 10 and a residual heat sensor 11 are arranged on the substrate 7. A voltage-measurement unit 12 is combined with the lambda sensor 8. A voltage source 13 and a current measurement unit 14 are combined with the $NO_x$-sensor 9. A further voltage source 15 and a further current-measuring unit 16 are associated with the oxygen sensor 10. The residual heat sensor 11 is connected to a measuring bridge, as will be described in detail below.

The voltage and current measuring units 12, 14, and 16, shown in FIG. 2 are only shown schematically and are included in the filter- and amplifier-circuit 3 (see FIG. 1) which thus constitutes a common measuring unit supplying the signal packet X to the analyzer unit 5.

Figure 3:
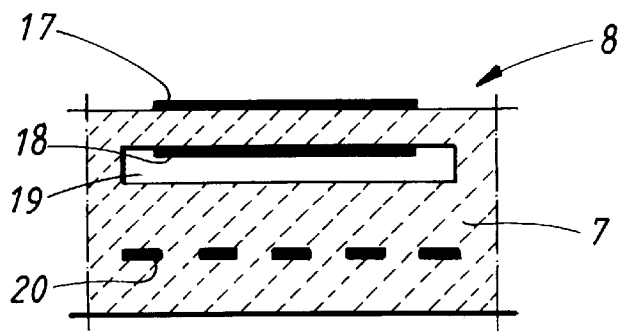
FIG. 3 is a side, sectional view of a lambda sensor used in accordance with the present invention.

FIG. 3 shows a cross-sectional view through the lambda probe 8. On the upper side of the substrate 7 there is a first electrode 17 which is composed of platinum. A second electrode 18, which functions as a reference electrode, is arranged within an air gap 19 which extends through the lambda probe 8. Additionally, there is a heating element 20 incorporated into the substrate 7. The heating element 20 is composed of an electrode, preferably of platinum or tungsten, which is connected to an external voltage source (not shown). The substrate 7 can be heated up to a correct working temperature (400° C.–800° C.) with the aid of the heating element 20. The potential difference between the two electrodes, 17 and 18, can be measured by connection (not shown) to the above-mentioned voltage measuring unit 12. The potential difference constitutes a measure of the lambda-ratio (i.e. rich or lean) of the gas which surrounds the lambda sensor 8.

Figure 4:
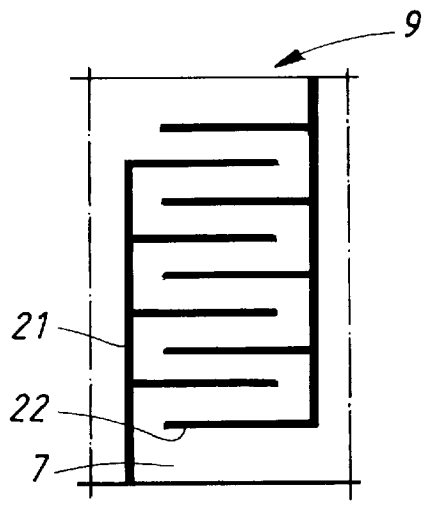
FIG. 4 is a top view of an $NO_x$ sensor used in accordance with the present invention.

FIG. 4 shows a view from above of the $NO_x$-sensor 9 which comprises two electrodes, 21 and 22, respectively, which constitute the cathode and anode, respectively. The electrodes, 21 and 22, or at least the cathode, are made of gold, in accordance with this embodiment. When the $NO_x$-sensor 9 is surrounded by a gas which contains $NO_x$-compounds, these will be adsorbed on the surface of the sensor 9, i.e. on the electrodes, 21 and 22, and the substrate 7. A selective dissociation, i.e. a decomposition, will occur thereafter so that negative oxygen ions, $O^-$, are formed at the cathode 21. With the assistance of the voltage applied by the voltage source 13 (see FIG. 1), the oxygen ions can be transported through the oxygen-ion-conductive substrate. Molecular oxygen, $O_2$, is formed at the anode 22, which oxygen desorbs from the $NO_x$-sensor's 9 surface back into the gas phase. At the same time as the oxygen atoms are ionized at the cathode 21, the nitrogen atoms recombine into molecular nitrogen, $N_2$, and return from the surface of the $NO_x$-sensor 9 into the gas phase.

In accordance with a further embodiment of the $NO_x$-sensor 9, only the anode 22 is made of gold. In this case the cathode 21 is made of platinum, for example.

With the aid of the above-mentioned current measuring unit 14 (see FIG. 1), the oxygen-ion current occurring in the circuit can be measured. This measured current thus constitutes a measure of the amount of $NO_x$-compounds in the gas stream.

Measuring with the $NO_x$-sensor 9 is selective, i.e. the oxygen ion current which occurs in the sensor 9 originates mainly from the $NO_x$-compounds included in the gas stream. The measuring of the $NO_x$-compounds in the $NO_x$-sensor 9 is thus substantially independent of the concentration of oxygen in the gas stream.

The selective function of the $NO_x$-sensor 9 is obtained by the formation of the substrate 7, which is oxygen-ion-conductive, and of the electrodes, 21 and 22, of which at least one is gold. Furthermore, the selectivity can be affected by the choice of pump voltage, i.e. with the aid of the voltage applied by the voltage source 13. The invention is therefore particularly suitable for measurements of $NO_x$-compounds in connection with exhaust gases in which the oxygen content varies, and gives a measurement which is substantially independent of the variations in the oxygen concentration of the exhaust gases.

During transport from the cathode 21 to the anode, the oxygen ions will primarily be displaced along the outer layer of the substrate 7. This provides a good time response during measurement with the $NO_x$-sensor 9.

In order that the transport of the oxygen ions occurs in an optimal manner, the respective electrodes, 21 and 22, are formed as a straight line with a number of transverse lines arranged so that they project substantially perpendicularly from the straight line. The two conductive patterns are arranged so that they "project into one another." This arrangement means that the interface between the electrodes, 21 and 22, the substrate 7, and the gas in which the sensor 9 is located, is made as large as possible. In this manner, transport of the negative oxygen ions can be maximized, which contributes to a high current through the $NO_x$-sensor 9. Additionally, it is most important that the distance between the electrodes 21 and 22 is as small as possible, which yields a short response time during measurements with the $NO_x$-sensor 9.

Figure 5:
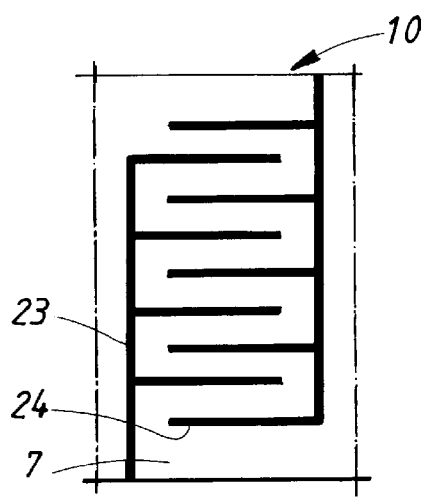
FIG. 5 is top view of an oxygen sensor used in accordance with the present invention.

FIG. 5 shows a view from above the oxygen sensor 10. A conductive pattern is arranged on the substrate 7, said pattern being in the form of two electrodes, 23 and 24, respectively. In the same way as the electrodes 21 and 22 of the aforementioned $NO_x$-sensor 9, the electrodes 23 and 24 of the oxygen sensor 10 are formed as a straight line with a plurality of transverse lines which project substantially perpendicularly from the straight line. The electrodes, 23 and 24, are preferably of platinum. By applying a voltage over the electrodes, 23 and 24 (with the aid of the voltage source 15 shown in FIG. 1), a current moves in the circuit in the presence of oxygen. This occurs due to the substrate 7 being conductive for oxygen ions at high temperatures (400° C.–800° C.). This oxygen-ion current can be measured with the aid of the current measuring unit 16 shown in FIG. 1. The size of the measured current is proportional to the oxygen concentration in the gas surrounding the oxygen sensor 10. In addition to oxygen, the oxygen sensor 10 is influenced by, for example, $NO_x$-compounds, hydrocarbons and hydrogen.

Figure 6:
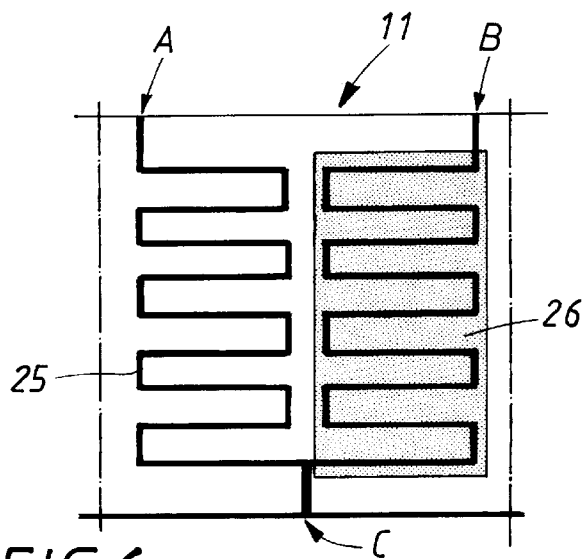
FIG. 6 is a top view of a residual heat sensor used in accordance with the present invention.

FIG. 6 shows the residual heat sensor 11 which is based on a so-called pellistor which is a type of sensor known (per se) from Swedish Patent Application No. 9301715-0. The residual heat sensor 11 comprises a conductive pattern 25 which forms two resistors, a first resistor AC which is formed by the conductive pattern between the points A and C, and a second resistor BC which is formed by the conductive pattern between the points B and C. The conductive pattern 25 is composed of platinum, and both of the resistors, AC and BC, have the same resistance at the same temperature.

Figure 7:
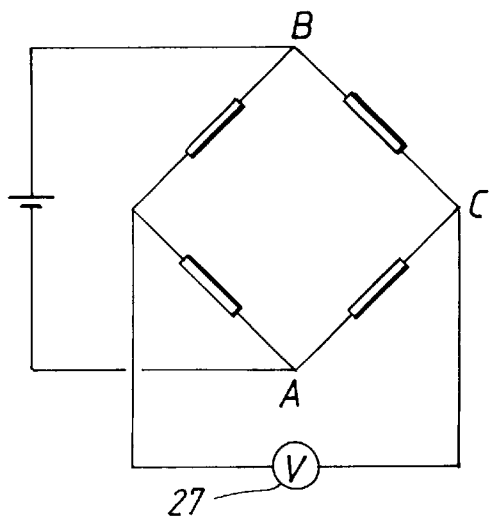
FIG. 7 is a schematic representation of Wheatstone-bridge intended to be used in connection with a residual heat sensor as shown in FIG. 6.

The resistance of the resistors AC and BC increases linearly with temperature. The first resistor AC is coated with a passive layer, preferably $AL_2O_3$, which is gas-tight, i.e. the surface of the conductive pattern cannot be influenced by the surrounding gas. The second resistor BC is coated with a catalytically active wash-coat 26. The hydrocarbons and the carbon monoxide will be burned on the active wash-coat 26 in the presence of oxygen. This combustion brings about a temperature increase in the first resistor BC which means that its resistance increases somewhat with respect to the resistance of the resistor AC. By coupling the resistances AC and BC in a so-called Wheatstone-bridge which is shown in FIG. 7, the small resistance changes which result from the combustion of the oxidizable substances on the wash-coat 26 can be detected. The denotations A, B, and C in FIG. 7 correspond to what is shown in FIG. 6.

The second resistance AC functions as a reference which is subjected to the same environment (ambient temperature, flow, air humidity, etc.) as the first resistor BC. This means that only the resistance change resulting from the combustion heat produces a resistance difference between the two resistors. With the aid of a voltage measuring unit 27, the voltage over the Wheatstone-bridge can be measured. This voltage is proportional to the residual heat in the gas, i.e. the amount of unburnt oxidizable substances in the gas.

The present invention can be used in applications having different exhaust gas compositions. In those cases where rich mixtures occur, the sensor unit 1 can be arranged in such a way that an electric voltage is connected over the ceramic oxygen-ion-conductive substrate, whereby one side of the substrate has access to the atmosphere and the other side of the substrate has access to the gas which is to be analyzed. In this manner, the necessary oxygen for complete combustion of the hydrocarbons and the carbon monoxide is supplied to the catalytically active wash-coat 26. In turn, this makes the measurements substantially independent of the oxygen content in the exhaust gases.

Figure 8:
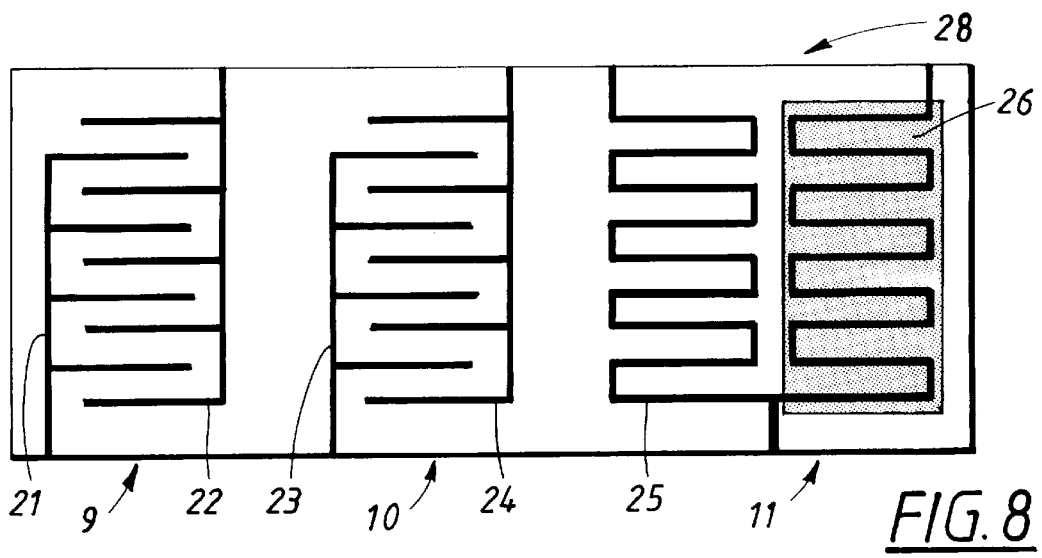
FIG. 8 is a top view of a sensor unit in accordance with one embodiment of the present invention for use in connection with diesel engines.
Figure 9:
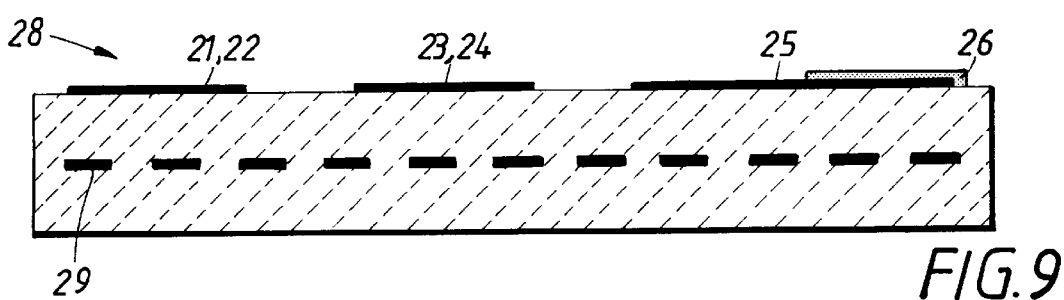
FIG. 9 is side, sectional view of the sensor unit shown in FIG. 8.

A particular application of the sensor unit according to the present invention is as a sensor for diesel exhaust gases. Such exhaust gases contain between about 5 and 20% oxygen, soot, nitrogen-oxides, carbon-oxides and hydrocarbons. FIG. 8 shows a view from above of a sensor unit 38 according to the present invention which comprises a $NO_x$-sensor 9, an oxygen sensor 10 and a residual heat sensor 11. FIG. 9 shows a side view of the same sensor unit 28. The $NO_x$-sensor 9 comprises, as described above, two electrodes, 21 and 22, of which at least one is gold. The oxygen sensor 10 comprises two electrodes, 23 and 24, of platinum. The residual heat sensor 11 comprises a conductive pattern 25 of platinum with a layer 26 of wash-coat and a passivating layer. As shown in FIG. 9, the sensor unit 28 comprises the heating element 29.

In accordance with a possible embodiment for analysis of diesel exhaust gases, the invention may include only one $NO_x$-sensor and a residual heat sensor, i.e. no oxygen sensor. This is possible in particular with heavy diesel vehicles having combustion engines, to which a predetermined amount of fuel and air is injected at a specific operating condition. Since the amount of fuel and air is known, the amount of oxygen in the exhaust gases can be determined with sufficiently high accuracy. In this case, this results in no separate oxygen sensor being necessary.

The sensor unit 28 can be used in order to determine the $NO_x$ and oxygen concentration and the amount of residual heat in the form of hydrocarbons and carbon monoxide in the exhaust gases. These signals can be used, for example, to alter the control of the diesel engine so as to reduce the emissions from the engine.

Figure 10:
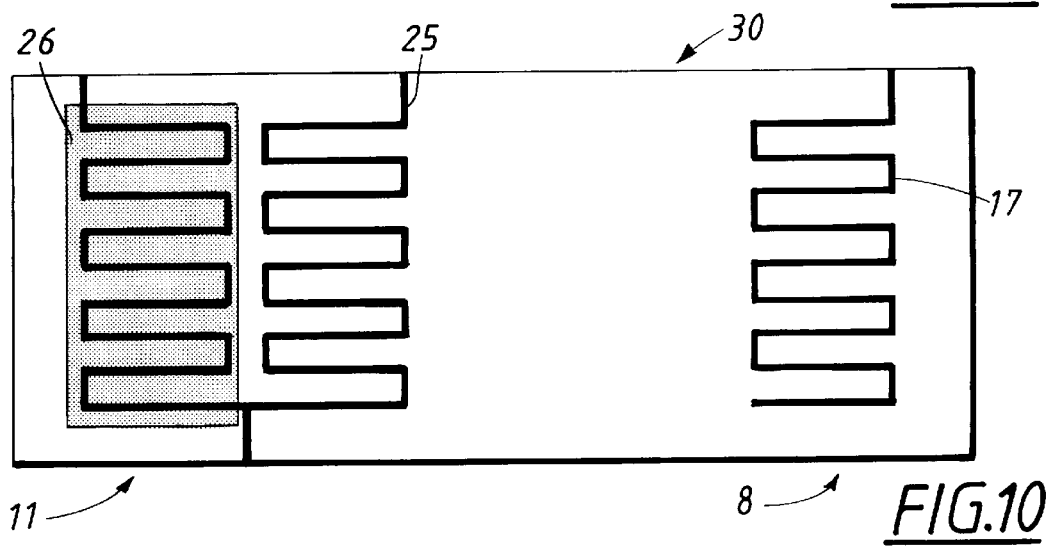
FIG. 10 is a top view of another embodiment of a sensor unit in accordance with the present invention.
Figure 11:
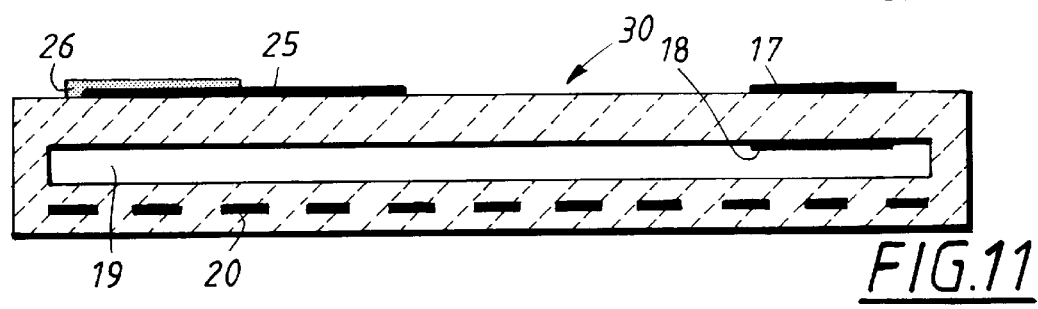
FIG. 11 is a side, sectional view of the sensor unit shown in FIG. 10.

In accordance with a further application of the present invention, this can be used in connection with diagnosis of a three-way exhaust catalyzer. Vehicles which are equipped with such a catalyzer must have an exhaust gas composition which is stoichiometric (i.e. lambda=1) for optimal conversion of the three exhaust gas components $NO_x$, CO and HC. With unknown requirements for cleaner cars, the catalyzer's effectiveness must be able to be diagnosed in the vehicle during operation (so-called "onboard diagnosis"). A sensor unit 30 in accordance with the present invention, which is shown in FIGS. 10 and 11 can, for this purpose, comprise a residual heat sensor 11 and a lambda sensor 8. The sensor unit 30 can be used both for regulating the engine control in order to achieve a maximum conversion of the three exhaust gas components and for diagnosing the catalyzer's effectiveness and absolute exhaust gas levels. The sensor unit 30 comprises a lambda sensor 8 with electrodes 17 and 18 and a residual heat sensor with a conductive pattern 25 as well as a wash-coat layer 26. The sensor unit 30 further comprises an air gap 19 and a heating element 20.

The sensor units 28 and 30 as shown in FIGS. 8–11 are connected to a filter- and amplifier-circuit and an analyzer circuit of the same type as mentioned above in connection with FIGS. 1 and 2.

Figure 12:
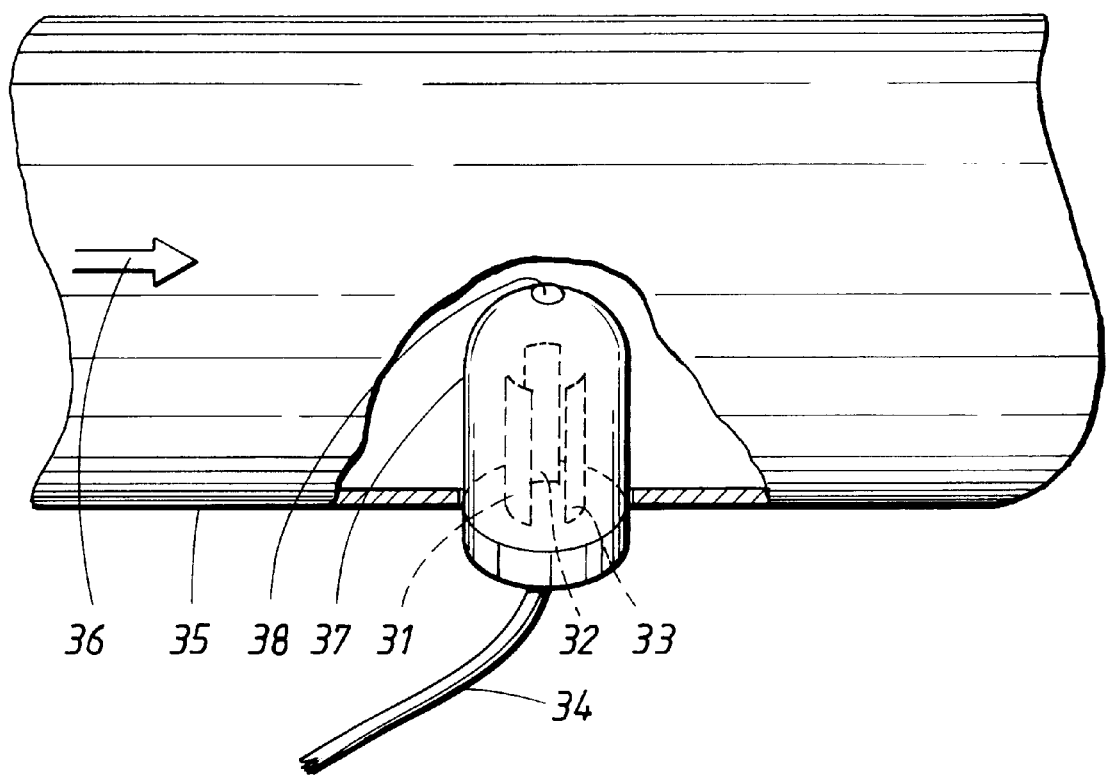
FIG. 12 is a partial, side, partially sectional view of a plurality of sensor units provided with a protective cap in accordance with the present invention.

The sensor units 1, 28 and 30 as described above are intended to be placed in the exhaust gas outlet of a motor vehicle. Instead of using only one sensor unit, a plurality of different sensor units can also be used, which can then be grouped together. The different sensor units can comprise different constellations of sensors which preferably constitute $NO_x$-sensors, lambda sensors, oxygen sensors and residual heat sensors. FIG. 12 shows such a group of sensor units, which in this case comprises three different sensor units 31, 32 and 33. The sensor units 31, 32 and 33 are joined with a measuring unit in the form of a filter- and amplifier-unit (see FIG. 1) by means of a common cable 34. The sensor units 31, 32 and 33 are arranged in the exhaust system 35 of a motor vehicle. The flow direction of the exhaust gases is indicated by arrow 36. The sensor units 31, 32 and 33 are preferably provided with a protective cap 37 which reduces the cooling effect which can be caused by the flowing exhaust gases, which means that a high and even temperature is obtained within the protective cap 37. The protective cap 37 is provided with at least one hole 38, or alternatively a slit or the like, so that the sensor units 31, 32 and 33 will be exposed to the exhaust gases. The hole 38 can be arranged in different ways, e.g. in the top of the protective cap 37.

According to a possible variation of the present invention, it can be provided with a so-called linear lambda sensor which is a sensor emitting a signal proportional to the oxygen concentration in the surrounding gas. The signal which is emitted is proportional to the oxygen concentration on the lean side and the rich side of $\lambda=1$. Such a linear lambda sensor can be arranged as a replacement for the above-mentioned oxygen sensor.

With the arrangement according to the present invention, a number of advantages are obtained. Firstly, a more exact value of, for example, $NO_x$-concentrations can be obtained if the values of HC and CO are known at the same time. Additionally, all of the sensors are subject to the same temperature if they are arranged at the same point. Furthermore, the combination of one or more sensors at one and the same point allows a system analysis by means of template-recognition of the neuro-net type.

For example, in the regulation of transients in an engine's operation it is important that the parameters are measured in the same time-window in the combustion process, which is achieved by the sensors being gathered at one and the same point. Furthermore, if the sensors are at the same point, the problems with calibration can be avoided, which otherwise could occur with sensors placed at different locations where the temperature and the gas composition are not the same.

An additional advantage is present in that the sensor unit according to the present invention only requires one attachment fixture, one cable, etc. Furthermore, an advantage is obtained in that the sensor unit uses a common, oxygen-ion-conductive substrate.

In addition, in accordance with alternative embodiments, the oxygen sensor 10 as well as the $NO_x$-sensor 9 can be formed with an air gap of similar type to the air gap 19 described above in connection with FIG. 3. This air gap functions as a reference chamber in which a first electrode, i.e. a reference electrode, is placed. A second electrode is arranged on the substrate and is subjected to the gas which is the object of measurement.

Furthermore, the oxygen sensor's 10 electrodes, 23 and 24, can be arranged on respective sides of the substrate 7. This is also valid for the $NO_x$-sensor's 9 electrodes 21 and 22.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. Apparatus for analyzing exhaust gases from a combustion process comprising at least one sensor unit mounted for direct contact with said exhaust gases, said at least one sensor unit comprising a plurality of sensor elements mounted on a common substrate for detecting specific gases contained in said exhaust gases and generating signals based thereon, wherein at least one of said sensor elements is a $NO_x$ sensor, said $NO_x$ sensor including an oxygen-ion transporter, said $NO_x$ sensor having an anode and a cathode, said cathode comprising a metal which is selective for the dissociation of nitrogen oxide as compared to oxygen, whereby said $NO_x$ sensor generates said signal based substantially only on the $NO_x$ content of said exhaust gases and substantially independent of the oxygen content of said exhaust gases, said substrate comprising an oxygen-ion-conductive ceramic material and said plurality of sensor elements comprising conductive patterns applied to said common substrate, and a common analyzer unit connected to said at least one sensor unit for analyzing said signals generated by said plurality of sensor elements.

2. The apparatus of claim 1 wherein said plurality of sensor elements in addition to the $NO_x$ sensor are selected from the group consisting of lambda sensors, oxygen sensors, and residual heat sensors.

3. The apparatus of claim 2 wherein said $NO_x$ sensor comprises:

an external voltage source connected to said anode and said cathode, said external voltage source being adapted to drive the current between said anode and said cathode; and measuring means for measuring said current connected to said anode and said cathode, whereby the measurement of said current corresponds to a measurement of the concentration of nitrogen oxides in the gas.

4. The apparatus of claim 3 wherein at least one of said anode and said cathode comprises gold.

5. The apparatus of claim 2 wherein said residual heat sensor comprises a first resistor including a surface exposed to said exhaust gases whereby said first resistor increases its temperature-dependent resistance when heated in the presence of oxidizable gas components in said exhaust gases, and a second resistor, a measuring bridge connected to said residual heat sensor, and a voltage source for supplying a voltage to said measuring bridge.

6. The apparatus of claim 5 wherein said second resistor comprises a reference for comparison with said resistance of said first resistor.

7. The apparatus of claim 2 wherein said plurality of sensor elements includes an associated air gap in said common substrate, a first electrode formed in said air gap, and a second electrode formed on said common substrate exposed to said exhaust gases.

8. The apparatus of claim 2 wherein said plurality of sensor units comprises a lambda sensor and a residual heat sensor, whereby said apparatus can be used for diagnosis of a catalyzer for purification of said exhaust gases.

9. The apparatus of claim 8 including an associated air gap within said common substrate, and an electrode associated with said lambda sensor arranged in said air gap.

10. The apparatus of claim 2 including a residual heat sensor whereby said apparatus can be used for analyzing said exhaust gases from a diesel engine.

11. The apparatus of claim 10 further comprising an oxygen sensor.

12. The apparatus of claim 1 wherein said common substrate comprises stabilized zirconium dioxide or titanium oxide.

13. The apparatus of claim 1 including heating means for heating said common substrate.

14. The apparatus of claim 13 wherein said heating means comprises a heating wire mounted in said substrate, and including a voltage source connected to said heating wire.

15. The apparatus of claim 1 including a protective cap substantially covering said at least one sensor unit.

* * * * *